US010247342B2

(12) United States Patent
Kesselaar et al.

(10) Patent No.: US 10,247,342 B2
(45) Date of Patent: Apr. 2, 2019

(54) CONNECTOR ASSEMBLIES, FLUID SYSTEMS INCLUDING CONNECTOR ASSEMBLIES, AND PROCEDURES FOR MAKING FLUID CONNECTIONS

(71) Applicant: Pall Corporation, Port Washington, NY (US)

(72) Inventors: Daniel Kesselaar, Hampshire (GB); Charles N. Rothwell, Surrey (GB); Richard Ballard, North Devon (GB); Danniel Bowdery, Portsmouth (GB)

(73) Assignee: Pall Corporation, Port Washington, NY (US)

( * ) Notice: Subject to any disclaimer, the term of this patent is extended or adjusted under 35 U.S.C. 154(b) by 481 days.

(21) Appl. No.: 15/085,042

(22) Filed: Mar. 30, 2016

(65) Prior Publication Data
US 2017/0284584 A1 Oct. 5, 2017

(51) Int. Cl.
F16L 17/06 (2006.01)
F16L 37/252 (2006.01)
(Continued)

(52) U.S. Cl.
CPC ........... *F16L 37/252* (2013.01); *A61M 39/18* (2013.01); *F16L 17/06* (2013.01); *F16L 37/113* (2013.01);
(Continued)

(58) Field of Classification Search
CPC .. F16L 2201/44; F16L 17/06; A61M 39/1011; A61M 39/14; A61M 2039/1027; A61M 39/165
(Continued)

(56) References Cited

U.S. PATENT DOCUMENTS 2,816,779 A 12/1957 Jensen
3,709,526 A 1/1973 Cromie
(Continued)

FOREIGN PATENT DOCUMENTS

CN 104364573 A 2/2015
DE 10 2013 214 068 A1 1/2015
(Continued)

OTHER PUBLICATIONS

Chinese Patent Office, Office Action in counterpart Chinese Application No. 201710213906.5, dated Aug. 27, 2018.
(Continued)

*Primary Examiner* — David Bochna
(74) *Attorney, Agent, or Firm* — Leydig Voit & Mayer

(57) ABSTRACT

A connector body for use in a connector assembly for making fluid connections includes a hollow connector body, the hollow connector body comprising a resilient deformable seal having a central aperture and a lip surrounding the central aperture; a locking mechanism integrally formed with the hollow connector body, the locking mechanism comprising at least one lug including a slot, and at least one ramp; a hollow connector first body end and a second body end; and an anti-actuation assembly engagement portion comprising at least one recess and/or at least one protrusion; and a removable anti-actuation assembly comprising at least one peel strip, and at least one recess and/or at least one protrusion, the at least one recess and/or at least one protrusion being engaged with the anti-actuation assembly engagement portion of the hollow connector body. Connector assemblies and processes for making fluid connections using the assemblies are also provided.

18 Claims, 14 Drawing Sheets

(51) Int. Cl.
*A61M 39/18* (2006.01)
*F16L 37/113* (2006.01)
*A61M 39/10* (2006.01)

(52) U.S. Cl.
CPC ...... *A61M 39/1011* (2013.01); *F16L 2201/10* (2013.01); *F16L 2201/44* (2013.01)

(58) Field of Classification Search
USPC .................................. 604/905, 256
See application file for complete search history.

(56) References Cited

U.S. PATENT DOCUMENTS

| | | | | |
|---|---|---|---|---|
| 4,019,512 | A * | 4/1977 | Tenczar | A61M 39/14 222/80 |
| 4,418,945 | A | 12/1983 | Kellogg | |
| 4,502,701 | A | 3/1985 | Treloar et al. | |
| 7,959,192 | B2 * | 6/2011 | Elton | A61M 39/10 137/614.03 |
| 8,029,023 | B2 * | 10/2011 | Arthun et al. | A61M 39/18 285/67 |
| 8,454,059 | B2 | 6/2013 | Stell | |
| 8,491,016 | B2 * | 7/2013 | Williams | F16L 37/30 285/352 |
| 9,770,581 | B2 * | 9/2017 | Gerst | F16L 37/113 |
| 2002/0011730 | A1 | 1/2002 | Stickan | |
| 2003/0030272 | A1 * | 2/2003 | Johnson | A61M 39/18 285/3 |
| 2010/0230961 | A1 * | 9/2010 | Johnson | F16L 37/0985 285/352 |
| 2013/0207380 | A1 * | 8/2013 | Williams | A61M 39/18 285/81 |
| 2015/0028586 | A1 | 1/2015 | Gerst et al. | |
| 2015/0260325 | A1 | 9/2015 | Quick | |
| 2016/0186906 | A1 | 6/2016 | Blake et al. | |

FOREIGN PATENT DOCUMENTS

| | | | |
|---|---|---|---|
| DE | 102013214068 A1 * | 1/2015 | ............ A61M 39/18 |
| EP | 2 428 718 A2 | 3/2012 | |
| FR | 3 007 816 A1 | 1/2015 | |
| JP | S57-150687 U | 9/1982 | |
| JP | S63-106990 U | 7/1988 | |
| JP | H10-281376 A | 10/1998 | |
| WO | WO 2012-077654 A | 6/2012 | |
| WO | WO 2013/123347 A1 | 8/2013 | |
| WO | WO 2013/162743 A1 | 10/2013 | |

OTHER PUBLICATIONS

European Patent Office, Extended European Search Report in counterpart European Application No. 17 16 2257, dated Jul. 31, 2017.

Intellectual Property Office of Singapore, Search Report in counterpart Singaporean Application No. 10201701914P, dated Oct. 13, 2017.

Japanese Patent Office, Office Action in counterpart Japanese Application No. 2017-043132, dated Sep. 4, 2018.

* cited by examiner

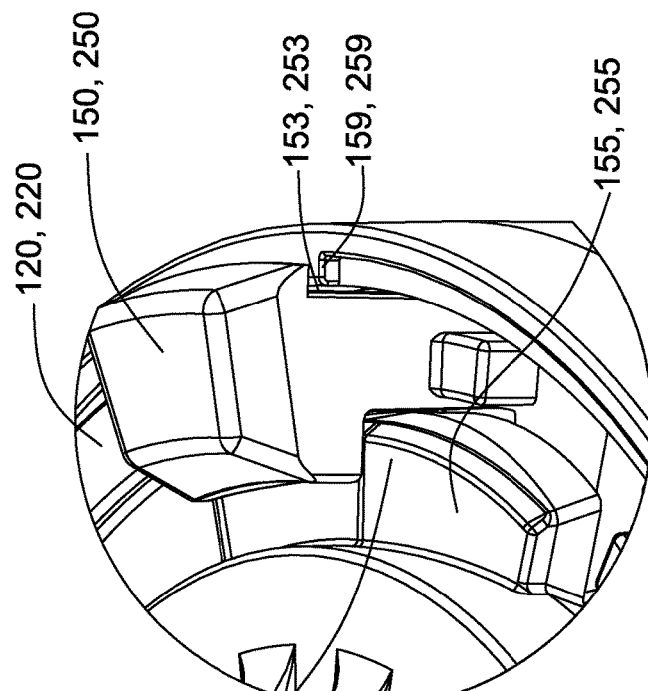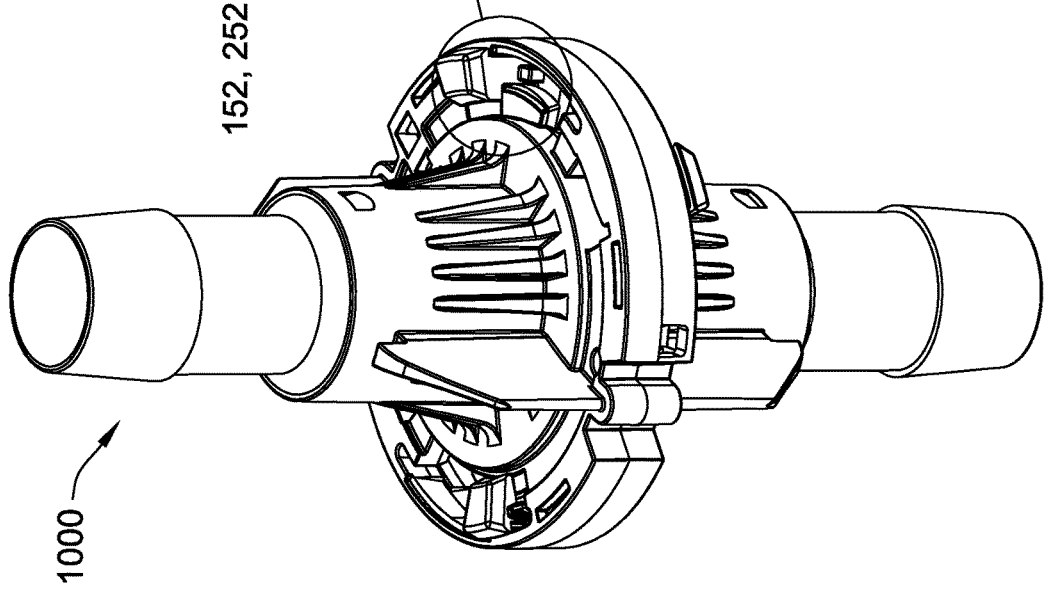

CONNECTOR ASSEMBLIES, FLUID SYSTEMS INCLUDING CONNECTOR ASSEMBLIES, AND PROCEDURES FOR MAKING FLUID CONNECTIONS

BACKGROUND OF THE INVENTION

The present invention is useful in many different industries, including the biopharmaceutical, biotechnology, food, beverage, cosmetic, and medical industries. In all of these industries, large or small systems of pipes, tubes, hoses and other conduits channel fluids from one location to another. The fluids may be gases, liquids, or mixtures of gases, liquids and/or solids. Many of these fluid systems, including biopharmaceutical and medical systems, transfer these fluids from one sterile location to another sterile location and have very strict requirements for sterility. The introduction into the fluid of unwanted contaminants, including biological contaminants, such as viruses or minute organisms, e.g., bacteria, and environmental contaminants, such as dust or dirt, can be highly detrimental for a great variety of reasons.

It is often necessary to make fluid connections in these systems, for example, to connect or disconnect existing conduits or components of the system, to install additional conduits for new fluid pathways, to add new components or replace existing components, or even to piece together an entirely new system. The present invention relates to connector assemblies and processes for making fluid connections. Connector assemblies and processes embodying the invention may include connector bodies and each connector body may have two ends. One end may be connected to a conduit or a component of the fluid system. The other end of the connector body may be coupled to the corresponding end of another connector body to make the fluid connection. Connector assemblies and processes embodying the invention allow this fluid connection to be made quickly and in a highly effective, reliable, and safe manner. Many embodiments further provide a sterile connection that resists the introduction of unwanted contaminants. Consequently, connector assemblies and processes embodying the invention are suitable for open, closed, and sterile closed fluid systems.

The present invention provides for ameliorating at least some of the disadvantages of the prior art. These and other advantages of the present invention will be apparent from the description as set forth below.

BRIEF SUMMARY OF THE INVENTION

An embodiment of the invention provides a connector assembly for making fluid connections comprising (a) a first hollow connector body, the first hollow connector body comprising a first resilient deformable seal having a central aperture and a lip surrounding the central aperture; a first locking mechanism integrally formed with the first hollow connector body, the first locking mechanism comprising at least one lug including a slot, and at least one ramp; a first hollow connector first body end and a first hollow connector second body end; (b) a second hollow connector body, the second hollow connector body comprising a second resilient deformable seal having a central aperture and a lip surrounding the central aperture; a second locking mechanism integrally formed with the second hollow connector body, the second locking mechanism comprising at least one lug including a slot, and at least one ramp; a second hollow connector first body end and a second hollow connector second body end; (i) wherein the first hollow connector body and the second hollow connector body contact each other in a first position, and when subsequently twisted together, the first resilient deformable seal seals against the first hollow connector body, and the second resilient deformable seal seals against the second hollow connector body, in a second position, the second position comprising an actuation position.

In another embodiment, a process for making fluid connections is provided, the method comprising (a) placing a first hollow connector body, the first hollow connector body comprising a first resilient deformable seal having a central aperture and a lip surrounding the central aperture; a first locking mechanism integrally formed with the first hollow connector body, the first locking mechanism comprising at least one lug including a slot, and at least one ramp; a first hollow connector first body end and a first hollow connector second body end, in contact with a second hollow connector body, the second hollow connector body comprising a second resilient deformable seal having a central aperture and a lip surrounding the central aperture; a second locking mechanism integrally formed with the second hollow connector body, the second locking mechanism comprising at least one lug including a slot, and at least one ramp; a second hollow connector first body end and a second hollow connector second body end, in a first position; and (b) twisting the first hollow connector body and/or the second hollow connector body such that the first locking mechanism engages with the second locking mechanism, the first resilient deformable seal seals against the first hollow connector body, and the second resilient deformable seal seals against the second hollow connector body, in a second position, the second position comprising an actuation position.

Another embodiment of the invention provides a connector body for use in a connector assembly for making fluid connections, the connector body comprising a hollow connector body, the hollow connector body comprising a resilient deformable seal having a central aperture and a lip surrounding the central aperture; a locking mechanism integrally formed with the hollow connector body, the locking mechanism comprising at least one lug including a slot, and at least one ramp; a hollow connector first body end and a hollow connector second body end; and an anti-actuation assembly engagement portion comprising at least one recess and/or at least one protrusion; a removable anti-actuation assembly comprising at least one peel strip, and at least one recess and/or at least one protrusion, the at least one recess and/or at least one protrusion being engaged with the anti-actuation assembly engagement portion of the hollow connector body; and, a removable cap, engaged with the hollow connector body, wherein the removable anti-actuation assembly is interposed between the cap and the hollow connector first body end, the cap covering the hollow connector first body end.

In other embodiments, fluid systems are provided, the systems comprising a bioprocessing unit connected to one or more of the connector bodies of the connector assembly.

BRIEF DESCRIPTION OF THE SEVERAL VIEWS OF THE DRAWING(S)

Figure 4:
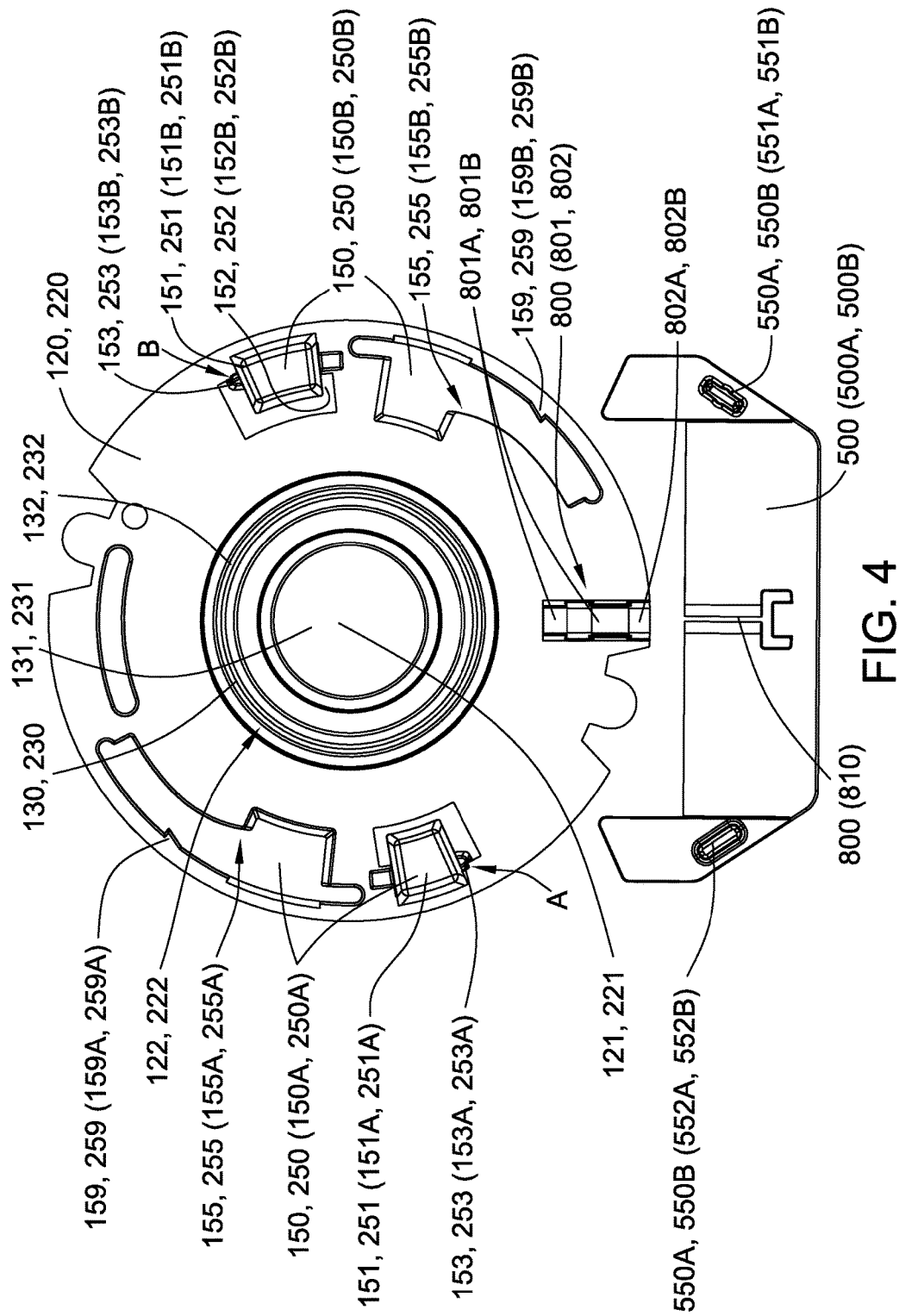

FIG. 4 is a first end view of a hollow connector body, also showing a groove containing a resilient deformable seal; a locking mechanism integrally formed with the hollow connector body, the locking mechanism comprising lugs including slots, and ramps; and a component of an alignment arrangement for engagement with the anti-actuation assembly, wherein the component comprises at least one recess (illustrated as two recesses) in the first end of a hollow connector body.

Figure 5A:
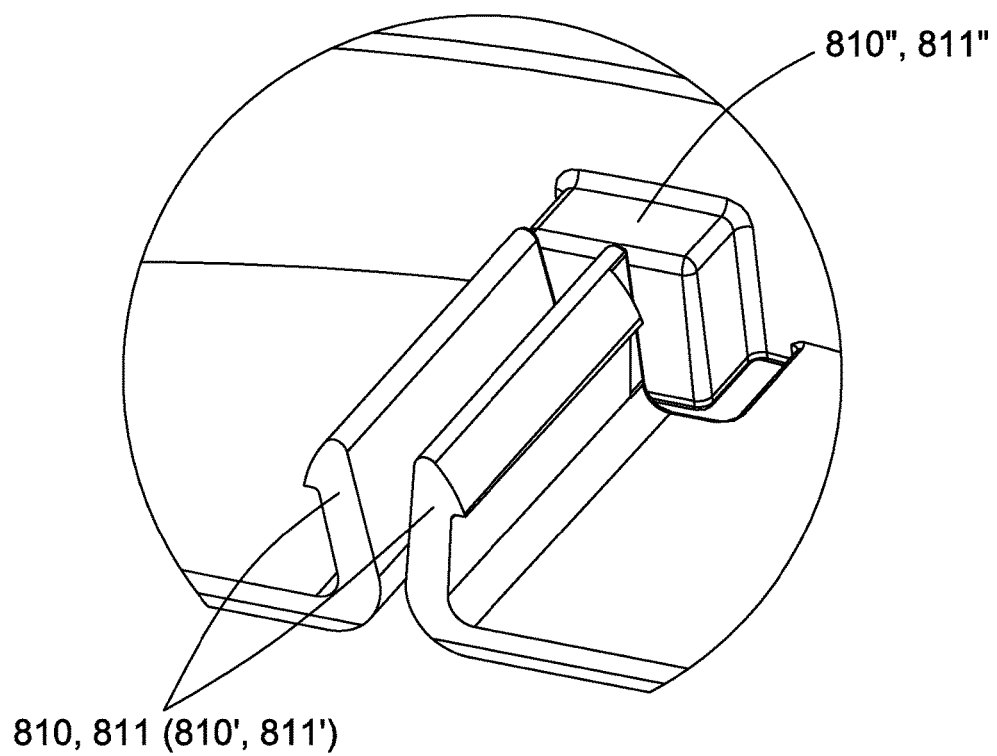
Figure 5B:
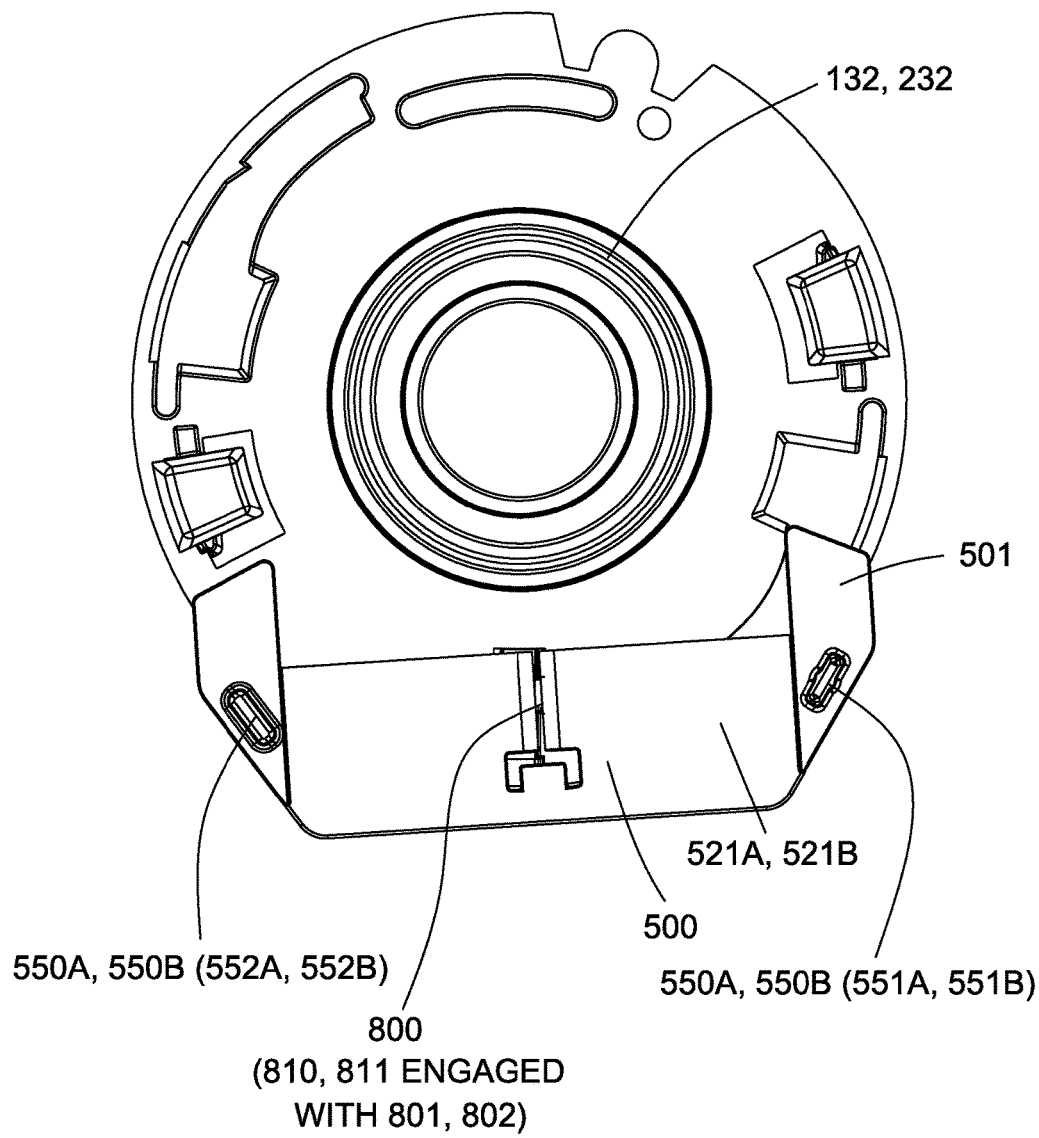

FIG. 5A shows an enlarged perspective view another component of the alignment arrangement comprising a protrusion (illustrated as two forms or types of protrusions) on a surface of the anti-actuation tab, the protrusion(s) being engageable with the recess(es) in the first end of the hollow connector body, allowing the surface of the anti-actuation assembly to mate with the hollow connector first body end. FIG. 5B shows the anti-actuation tab engaged with the first end of a hollow connector body via the alignment arrangement.

Figure 6:
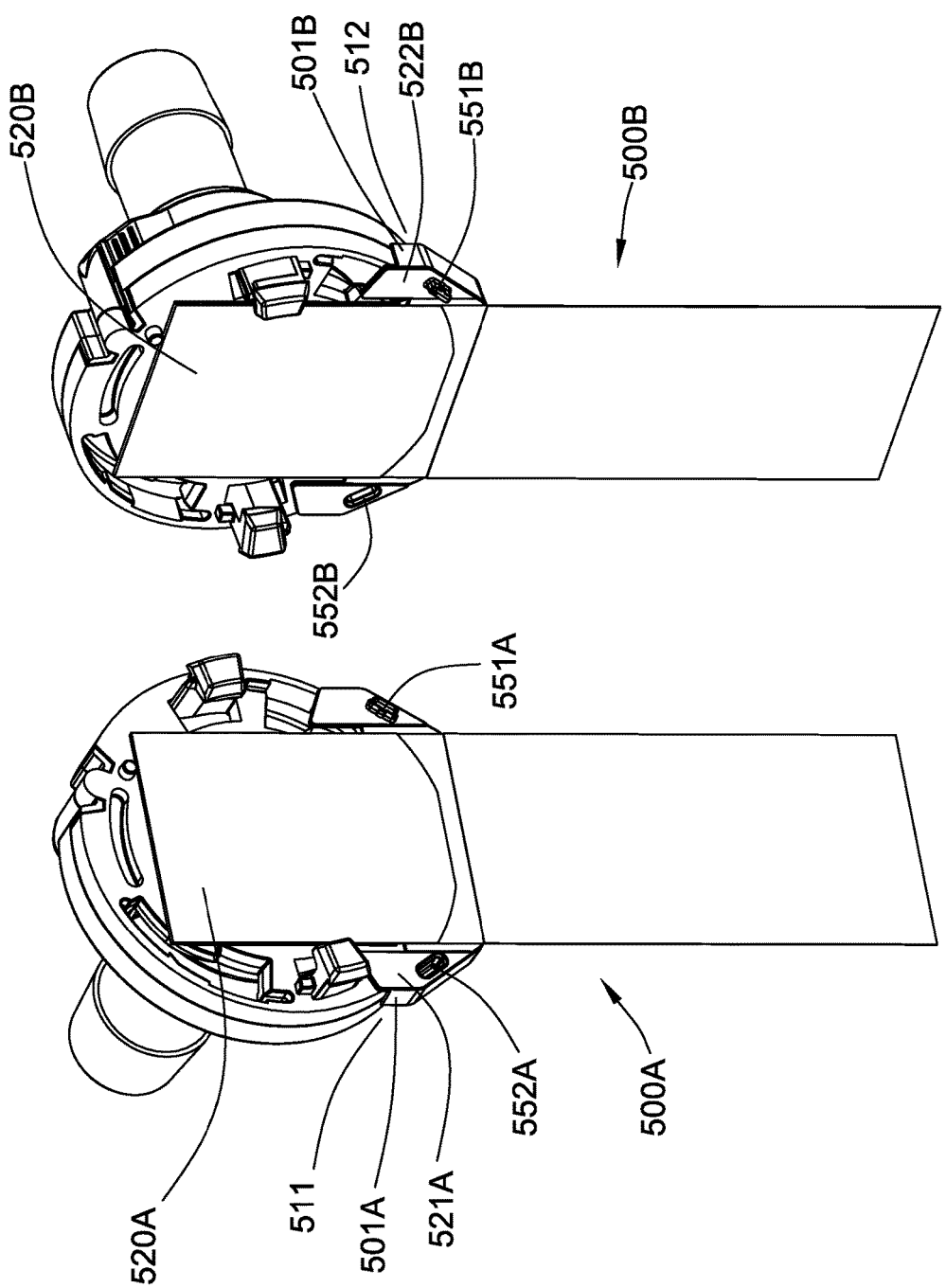

FIG. 6 shows separate first and second hollow connector bodies, and first and second anti-actuation subassemblies engaged with the respective hollow connector bodies, wherein each subassembly includes a subassembly keying arrangement comprising a protrusion and a recess, allowing the subassemblies to be mated together when the first and second hollow connector bodies contact each other in the first position.

FIG. 7A shows a perspective view of a connector assembly (without body covers) showing a ramp of the locking mechanism of one hollow connector body engages with the slot in the lug of the locking mechanism of the other hollow connector body.

FIG. 7B is an enlarged partial perspective view of the connector assembly shown in FIG. 7A, showing one hollow connector body's locking mechanism comprising a ramp engaging with the slot in the lug in the other hollow connector body's locking mechanism as at least one of the connector bodies moves from the first position to the second position.

Figure 8:
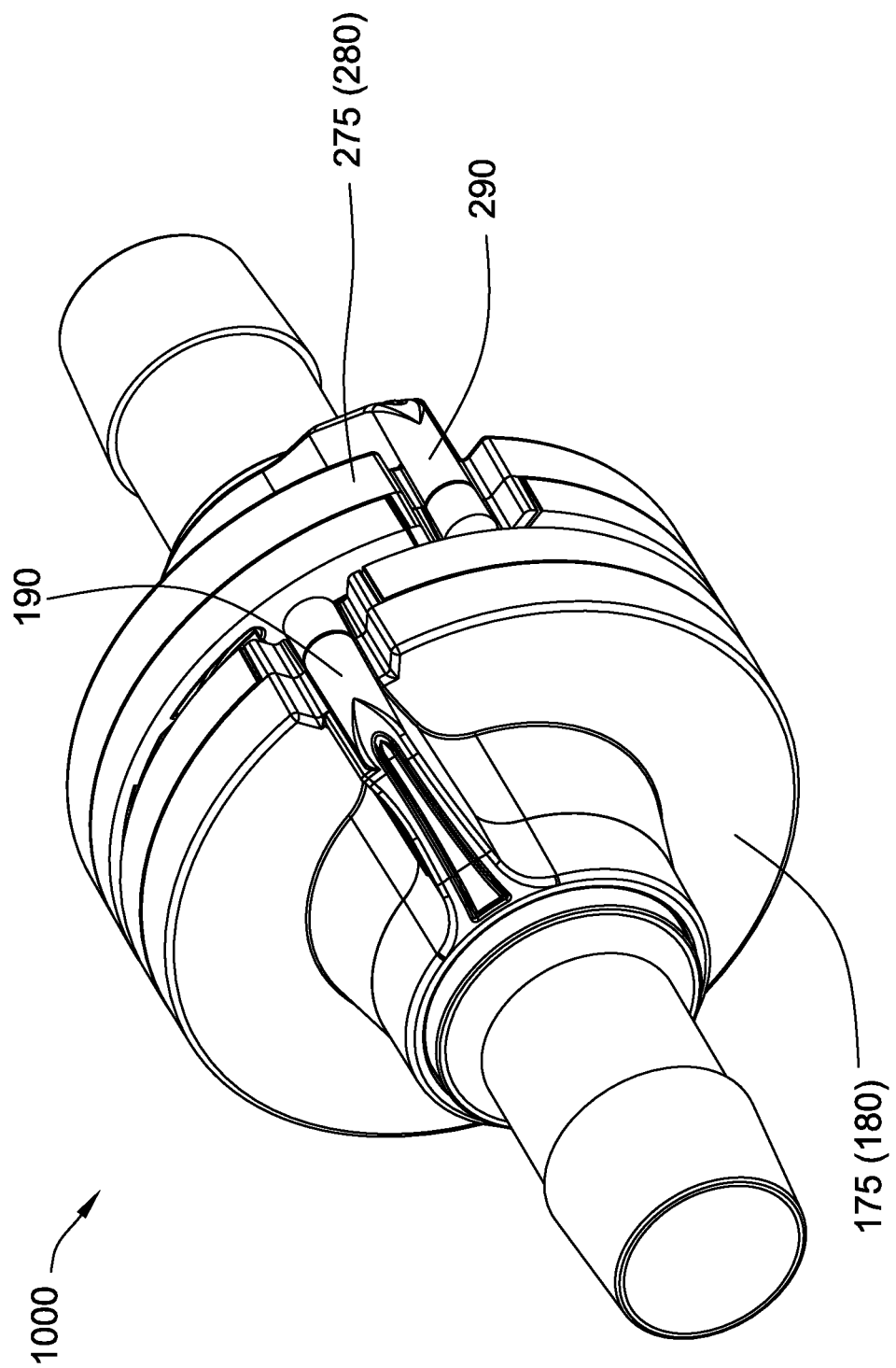

FIG. 8 is a perspective view of an embodiment of the connector assembly, also showing body covers including external surfaces including alignment indicators, wherein first and second alignment indicators are in the first position, and are not aligned.

Figure 9A:
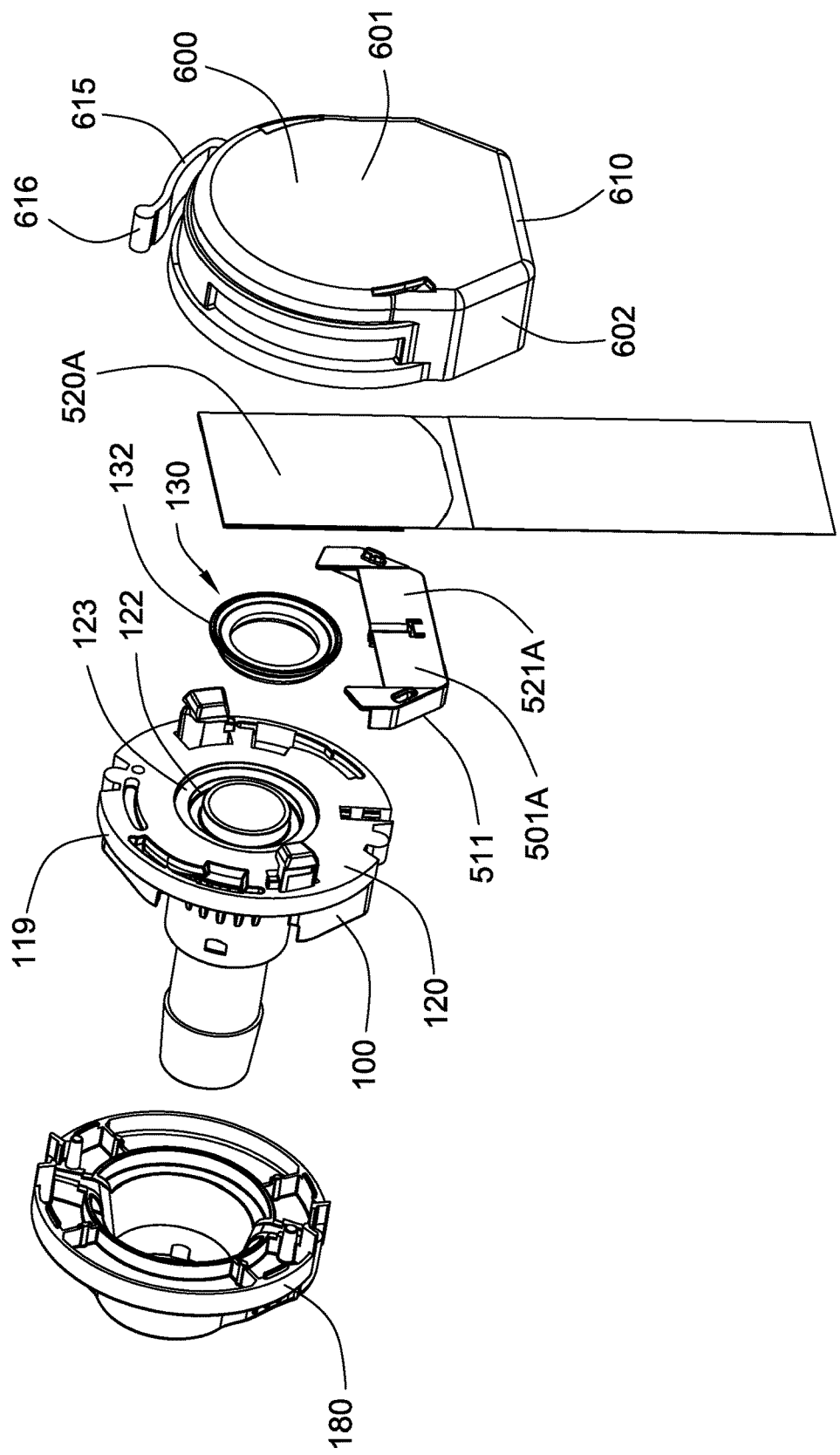
Figure 9B:
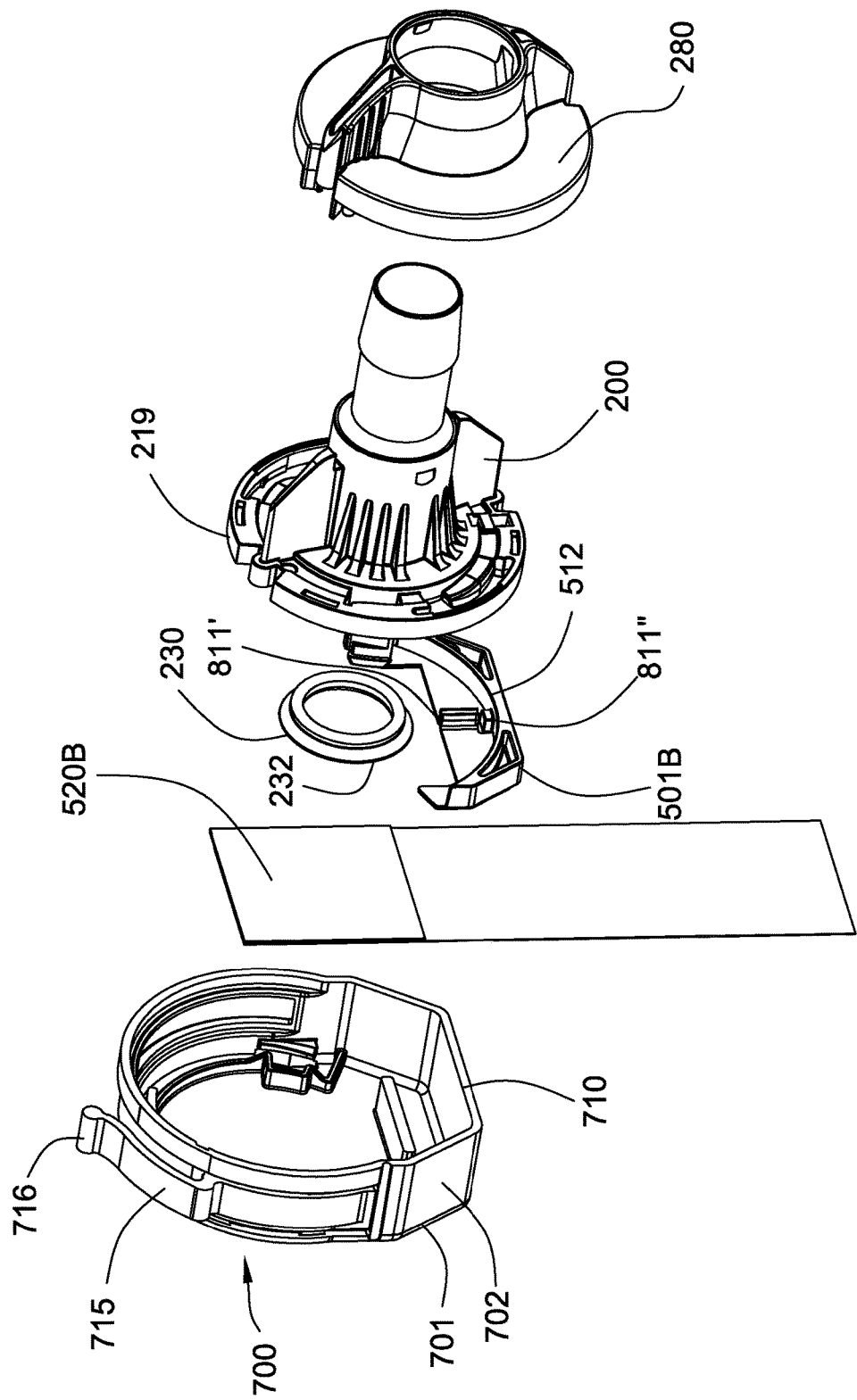

FIG. 9A shows an exploded view of a first hollow connector body, as well as a first hollow connector body cover, a first anti-actuation subassembly; and a first cap, the cap including a tear strip. FIG. 9B shows an exploded view of a second hollow connector body, as well as a second hollow connector body cover, a second anti-actuation subassembly; and a second cap, the cap including a tear strip.

Collectively, FIGS. 9A and 9B show an exploded view of an embodiment of a connector assembly.

Figure 10:
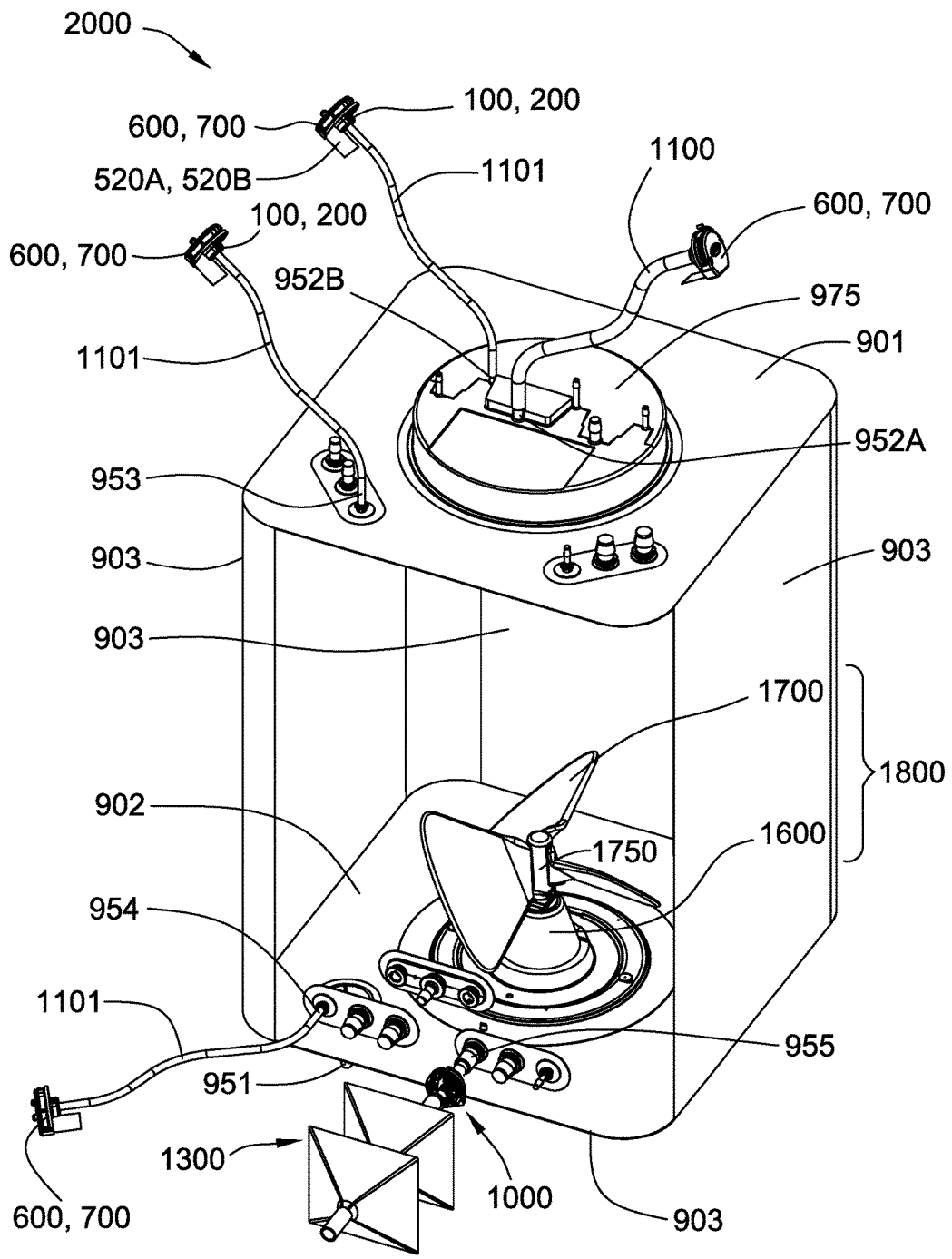

FIG. 10 shows illustrative multiple possible connections of embodiments of the connector assembly connected to a representative bioreactor or bioprocessing unit, wherein different connector assemblies can be used in different connections.

DETAILED DESCRIPTION OF THE INVENTION

In accordance with an embodiment of the present invention, a connector assembly for making fluid connections is provided, the connector assembly comprising: (a) a first hollow connector body, the first hollow connector body comprising a first resilient deformable seal having a central aperture and a lip surrounding the central aperture; a first locking mechanism integrally formed with the first hollow connector body, the first locking mechanism comprising at least one lug including a slot, and at least one ramp; a first hollow connector first body end and a first hollow connector second body end; (b) a second hollow connector body, the second hollow connector body comprising a second resilient deformable seal having a central aperture and a lip surrounding the central aperture; a second locking mechanism integrally formed with the second hollow connector body, the second locking mechanism comprising at least one lug including a slot, and at least one ramp; a second hollow connector first body end and a second hollow connector second body end; (i) wherein the first hollow connector body and the second hollow connector body contact each other in a first position, and when subsequently twisted together, the first resilient deformable seal seals against the first hollow connector body, and the second resilient deformable seal seals against the second hollow connector body, in a second position, the second position comprising an actuation position.

In another embodiment, a process for making fluid connections is provided, the method comprising (a) placing a first hollow connector body, the first hollow connector body comprising a first resilient deformable seal having a central aperture and a lip surrounding the central aperture; a first locking mechanism integrally formed with the first hollow connector body, the first locking mechanism comprising at least one lug including a slot, and at least one ramp; a first hollow connector first body end and a first hollow connector second body end, in contact with a second hollow connector body, the second hollow connector body comprising a second resilient deformable seal having a central aperture and a lip surrounding the central aperture; a second locking mechanism integrally formed with the second hollow connector body, the second locking mechanism comprising at least one lug including a slot, and at least one ramp; a second hollow connector first body end and a second hollow connector second body end, in a first position; and (b) twisting the first hollow connector body and/or the second hollow connector body such that the first locking mechanism engages with the second locking mechanism, the first resilient deformable seal seals against the first hollow connector body, and the second resilient deformable seal seals against the second hollow connector body, in a second position, the second position comprising an actuation position.

Embodiments of the method can further comprise removing an anti-actuation assembly comprising at least one peel strip, interposed between the first hollow connector first body end and the second hollow connector first body end, after (a) and before (b).

Yet another embodiment of the invention provides a connector body for use in a connector assembly for making fluid connections, the connector body comprising a hollow connector body, the hollow connector body comprising a resilient deformable seal having a central aperture and a lip surrounding the central aperture; a locking mechanism integrally formed with the hollow connector body, the locking mechanism comprising at least one lug including a slot, and at least one ramp; a hollow connector first body end and a hollow connector second body end; and an anti-actuation assembly engagement portion comprising at least one recess and/or at least one protrusion; a removable anti-actuation assembly comprising at least one peel strip, and at least one recess and/or at least one protrusion, the at least one recess and/or at least one protrusion being engaged with the anti-actuation assembly engagement portion of the hollow connector body; and, a removable cap, engaged with the hollow connector body, wherein the removable anti-actuation assembly is interposed between the cap and the hollow connector first body end, the cap covering the hollow connector first body end.

In an embodiment of the connector assembly, the assembly further comprise a removable anti-actuation assembly comprising at least one peel strip, interposed between the first hollow connector first body end and the second hollow connector first body end, wherein, when the first hollow connector body and the second hollow connector body contact each other in the first position, the anti-actuation assembly, when present, prevents forming the actuation position of the connector assembly, and when removed, allows forming the actuation position of the connector assembly.

In an embodiment, the anti-actuation assembly comprises a first surface facing the first hollow connector first body end and a second surface facing the second hollow connector first body end; and the connector assembly further comprises an alignment arrangement for mating the anti-actuation assembly with the first connector hollow body and the second hollow connector body, the alignment arrangement comprising protrusions and recesses; wherein the first and second surfaces of the anti-actuation assembly, the first hollow connector first body end, and the second hollow connector first body end each have at least one protrusion and/or at least one recess, such that the first surface of the anti-actuation assembly mates with the first hollow connector first body end, and the second surface of the anti-actuation assembly mates with the second hollow connector first body end.

If desired, the anti-actuation assembly comprises a first anti-actuation subassembly comprising the first surface of the anti-actuation assembly, and a first peel strip; and, a second anti-actuation subassembly comprising the second surface of the anti-actuation assembly, and a second peel strip. In some embodiments, the first anti-actuation subassembly and the second anti-actuation subassembly are mated together when the first hollow connector body and the second hollow connector body contact each other in the first position.

In an embodiment of the connector assembly, the first hollow connector body comprises a first connector external surface further comprising a first alignment indicator; and the second hollow connector body comprises a second connector external surface further comprising a second alignment indicator; the first alignment indicator and the second alignment indicator aligning when the first hollow connector body and the second hollow connector body are in the actuation position.

In a preferred embodiment, the connector assembly comprises a genderless connector assembly, wherein the connectors are neither "male" nor "female."

In other embodiments, fluid systems are provided, the systems comprising a bioprocessing unit connected to one or more of the connector bodies of the connector assembly. For example, a fluid system comprises an embodiment of the connector assembly, in fluid communication with a bioprocessing unit, the bioprocessing unit comprising a biocontainer having at least one wall including at least one port, an interior volume and including an impeller, wherein one of the first and second hollow connector bodies is in fluid communication with the port.

Embodiments of the invention are particularly suitable for single use technology (SUT) applications. Preferably, the connector assembly is a genderless connector assembly, i.e., not requiring male and female connections. Advantageously, any connector body can be connected to any other connector body. Additionally, the first and second hollow bodies can be identical, thus reducing production costs. If desired, connector bodies can be color coded (e.g., using colored covers fitted on the hollow bodies), allowing system customization and identification, which can reduce connection errors, including multi-connection errors (e.g., bioreactors can including a plurality of connections, such as fluid inlet ports, drain ports, sampling ports, vent ports, etc.), wherein the colors can provide a visual labeling guide for the various connections.

Each of the components of the invention will now be described in more detail below, wherein like components have like reference numbers.

Figure 1A:
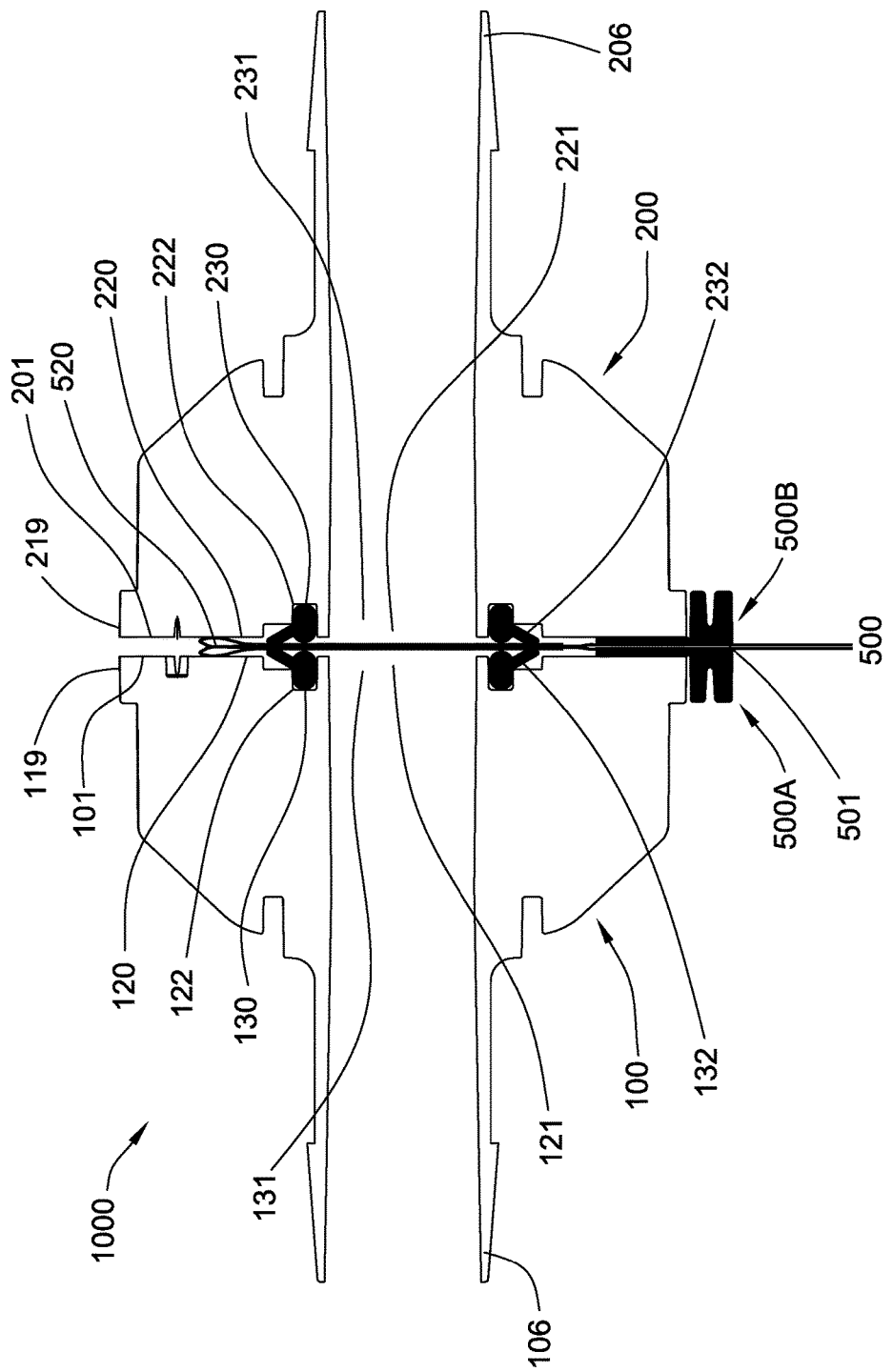
FIG. 1A is cross sectional view of an embodiment of a connector assembly comprising first and second hollow connector bodies contacting each other in a first position, and a removable anti-actuation assembly interposed between the connector bodies.
Figure 1B:
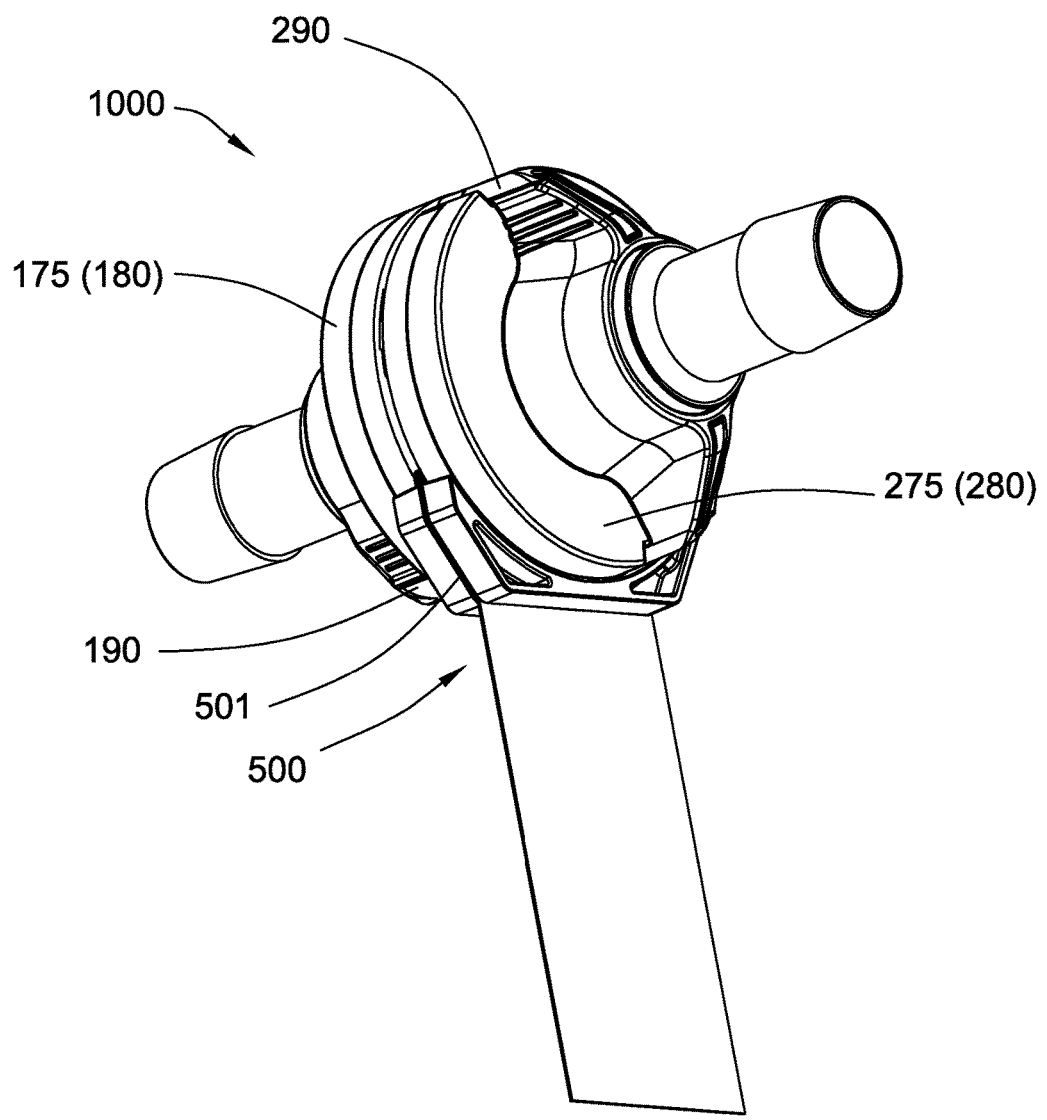
FIG. 1B is a perspective view of the connector assembly shown in FIG. 1A.

Connector assemblies embodying the invention may be configured in a wide variety of ways, and one of many different examples is shown in FIGS. 1A and 1B. The exemplary connector assembly 1000 comprises first and second hollow connector bodies 100, 200, wherein each connector body 100, 200 has first and second ends 101, 106; 201, 206 respectively, the first connector body first end 101 having a rim 119, a face 120 and a central opening 121, and the second connector body first end 201 having a rim 219, a face 220 and an opening 221. Each face includes a groove 122, 222 concentrically surrounding the opening 121,221, with a resilient deformable seal 130,230 having a central aperture 131,231 and a lip 132,232 surrounding the central aperture.

The connector bodies 100, 200 may be coupled to one another at their first ends 101, 201 by (using FIGS. 2A, 4, and 7 for reference) respective locking mechanisms (first locking mechanism 150; second locking mechanism 250), the respective locking mechanisms comprising a lug 151, 251 extending above the face, the lug including a slot 152, 252, and a guide 153, 253; and a ramp 155, 255 extending below the face. In some embodiments, the locking mechanisms each include a guide 153, 253 on the lug, and a spring arm 159, 259. In the embodiment illustrated in FIGS. 2A, 4, and 7, the first connector body includes first locking mechanisms 150A, 150B, including lugs 151A, 151B, slots 152A, 152B, guides 153A, 153B, ramps 155A, 155B, and spring arms 159A, 159B; and the second connector body includes second locking mechanisms 250A, 250B, including lugs 251A, 251B, slots 252A, 252B, guides 253A, 253B, ramps 255A, 255B, and spring arms 259A, 259B. The locking mechanism is integrally formed with the body, and as such, does not move separately from the rest of the body when the body moves from the first position to the second position.

Figure 2A:
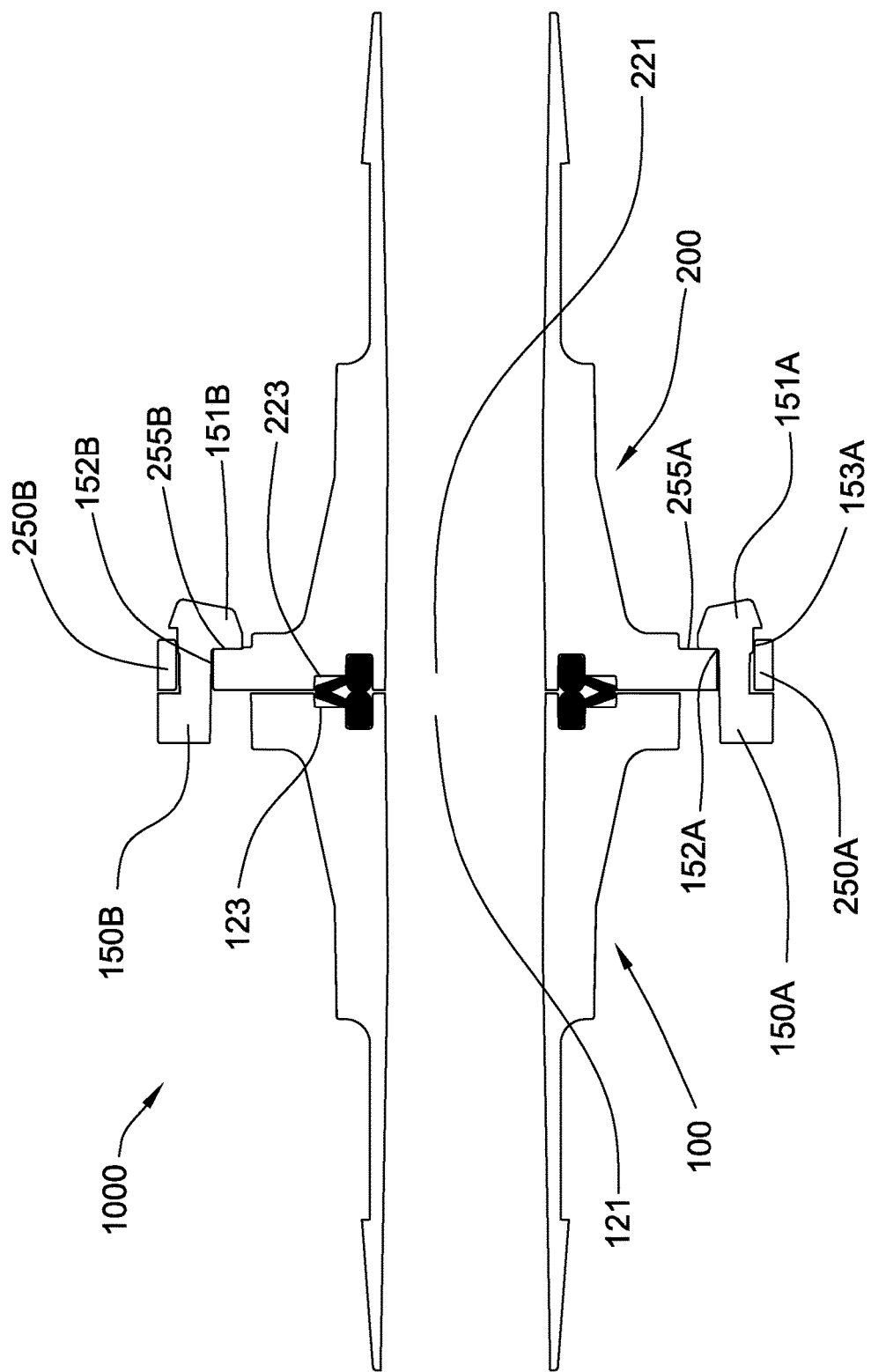
FIG. 2A is cross sectional view of the embodiment of the connector assembly shown in FIG. 1A, wherein the anti-actuation assembly has been removed, the connector bodies are in a second position (actuation position), and a first resilient deformable seal seals against the first hollow connector body, and a second resilient deformable seal seals against the second hollow connector body.
Figure 2B:
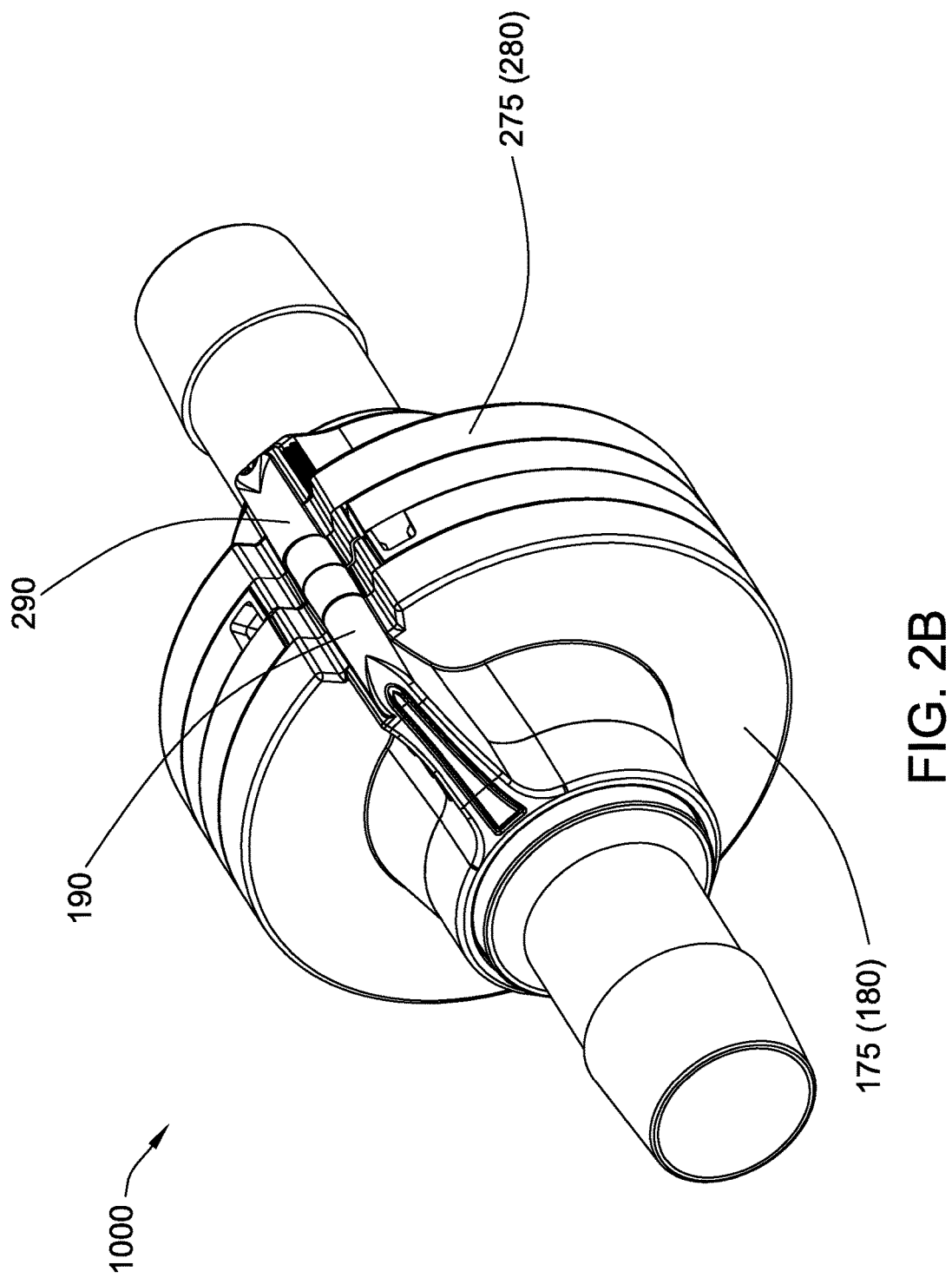
FIG. 2B is a perspective view of the connector assembly shown in FIG. 2A, also showing body covers including external surfaces including alignment indicators, wherein the first and second alignment indicators are aligned, showing that the first hollow connector body and the second hollow connector body are in the second (actuation) position.

As will be discussed in more detail below (e.g., as shown in FIGS. 2A, 2B, and 7), after an anti-actuation assembly 500 is removed, either or both of the hollow connector bodies can be rotated from a first position such that the ramp(s) of the locking mechanism(s) of one hollow connector body engages with the slot(s) in the lug(s) of the locking mechanism(s) of the other hollow connector body, until the hollow bodies are in a second (actuation) position. Once the bodies are in the actuation position, the interiors of the connector bodies fluidly communicate with one another through the coaxially aligned openings 121,221, preferably, in a sterile manner free of any external contamination.

Optionally, and as shown in FIGS. 7A and 7B, (a) the surface of the ramp and the surface of the slot that will contact the surface of the ramp have initial angles, and then level, such that the lugs stop on a level surface, providing a desired amount of pressure on the main bodies of the seals, when the connector bodies are in the actuation position, and/or (b), as shown particularly in FIGS. 4 and 5B, the locking mechanism has a spring arm 159 (159A, 159B), 259 (259A, 259B) that flexes to allow the lug guide 153 (153A, 153B), 253 (253A, 253B) to deflect it and return once the lug has passed, retaining the lug in the actuation position, preferably while providing a tactile and/or audible "click." Using FIG. 4B for reference, "A" and "B" indicate where the spring arm has returned after flexing, providing a tactile and/or audible "click."

The embodiment of the connector assembly 1000 shown in FIG. 1 also includes a removable anti-actuation assembly 500 comprising a tab 501 having a first surface 511 (facing the first hollow connector first body end) and a second surface 512 (facing the second hollow connector first body end), and a peel strip 520, interposed between the first hollow connector first body end and the second hollow connector first body end, wherein, when the first hollow connector body and the second hollow connector body contact each other in the first position, the anti-actuation assembly, when present, prevents forming the actuation position of the connector assembly, and when removed (as shown in FIG. 2), allows forming the actuation position of the connector assembly. If desired, the tab can include a pull ring.

In some embodiments, the connector assembly comprises an alignment arrangement for mating the anti-actuation assembly with the first connector hollow body and the second hollow connector body, the alignment arrangement comprising protrusions and recesses; wherein the first and second surfaces of the anti-actuation assembly, the first hollow connector first body end, and the second hollow connector first body end each have at least one protrusion and/or at least one recess, such that the first surface of the anti-actuation assembly mates with the first hollow connector first body end, and the second surface of the anti-actuation assembly mates with the second hollow connector first body end.

For example, in the embodiment shown in FIGS. 3, 4, 5A, and 5B, the connector assembly further comprises an alignment arrangement 800, including a recess 801 in the first end 101 of the first hollow connector body and a recess 802 in the first end 201 of the second hollow connector body (the illustrated recesses are each shown with 2 slots, 801A, 801B; 802A, 802B), and a protrusion 810 (shown as having 2 snap hooks 810' and a pin 810") on the first surface 511 of the anti-actuation tab 501, the protrusion being engageable with the recess 801, and a protrusion 811 (shown as having 2 snap hooks 811' (engageable with 801B) and a pin 811" (engageable with 802B)) on the second surface 512 of the anti-actuation tab 501), the protrusion being engageable with the recess 802. In some embodiments including pins, the engagement of the pins with the recesses further reduces flexing/movement when the subassemblies are engaged with the respective hollow bodies.

Figure 3:
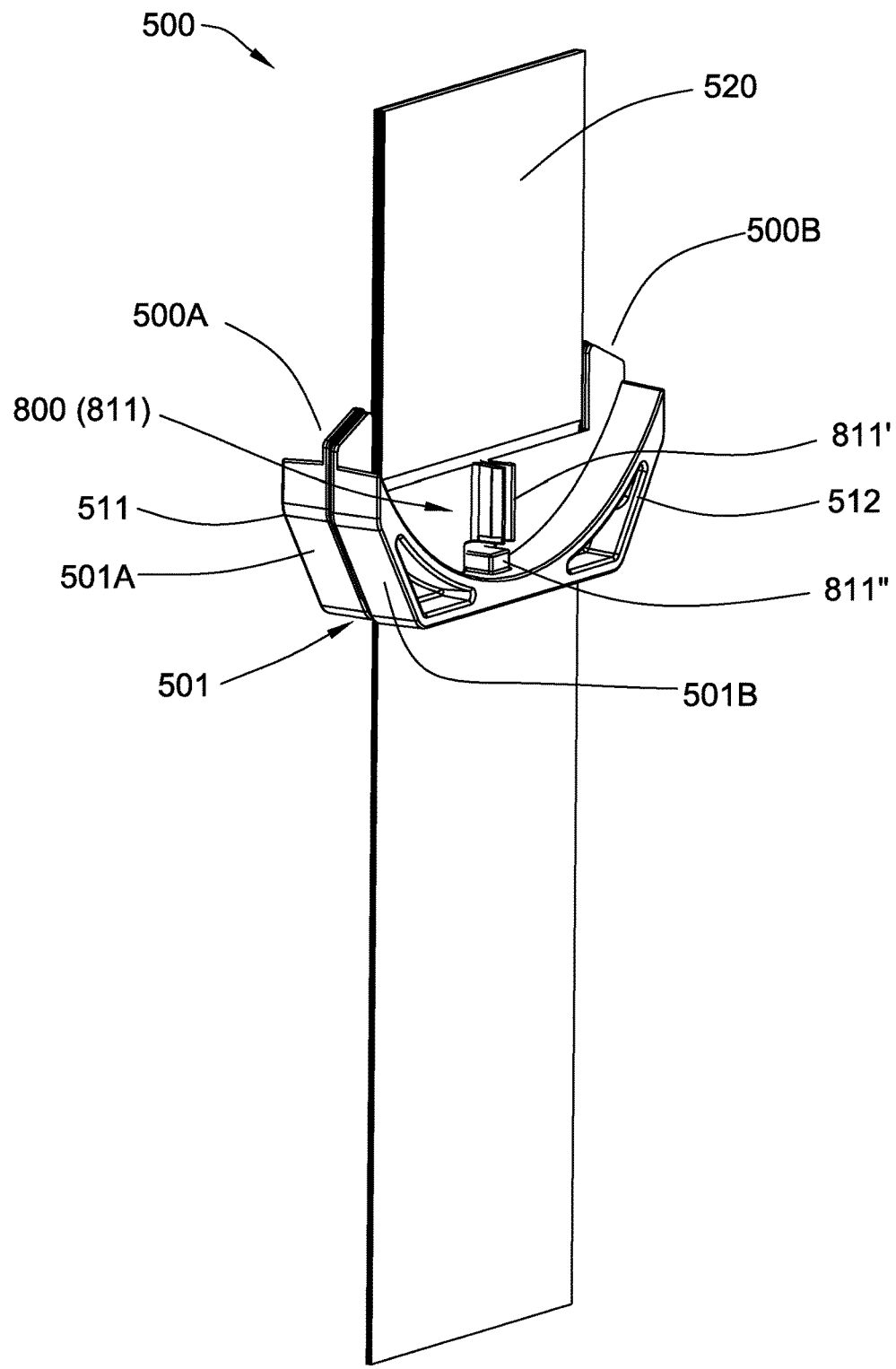
FIG. 3 is a perspective view of an anti-actuation assembly comprising a tab and a peelable strip.

In some embodiments, e.g., as shown in FIGS. 3 and 6, anti-actuation assembly 500 comprises first anti-actuation subassembly 500A comprising a subassembly tab 501A including the first surface 511, and a first peel strip 520A; and, a second anti-actuation subassembly 500B comprising a subassembly tab 501B including the second surface 512, and a second peel strip 520B. If desired, each subassembly can comprise a keying arrangement comprising at least one protrusion and at least one recess so that the first anti-actuation subassembly and the second anti-actuation subassembly can be mated together when the first hollow connector body and the second hollow connector body contact each other in the first position. For example, as shown in FIGS. 4 and 5B, subassembly tab 501A has a second surface 521A including a keying arrangement 550A comprising a protrusion 551A and a recess 552A, and subassembly tab 501B has a second surface 522B including a keying arrangement 550B comprising a protrusion 551B and a recess 552B, wherein protrusion 551A can be mated with recess 552B, and protrusion 551B and be mated with recess 551A. Advantageously, this allows the operator to pull either or both tabs 501A, 501B and/or either or both peelable strips 520A, 520B and remove the anti-actuation assembly from the connector assembly, so that the hollow connector bodies can be placed in the actuation position.

To enhance the sterility of the interiors of the connector bodies, peel strips (seal layers) are preferably arranged to cover the openings at the first ends of the connector bodies. The peel strips may be variously configured. Typically, the peel strip(s) are joined (e.g., welded, trapped, or clamped) to the anti-actuation assembly tab(s) and/or the faces of the hollow connector bodies. Preferably, peel strips are joined to the respective subassembly tabs and the hollow connector body faces (also covering the seals and contacting the seal lips). For many embodiments, the peel strip(s) may also cover all or at least a portion of the face seals without being joined to the seals. For example, each peel strip may completely cover at least the seal closest to the openings. The peel strip may not be joined to the seals themselves but may be joined to the surface of the face surrounding each seal.

The peel strip may be made from an impermeable material or a permeable material that resists the passage of contaminants, including biological containments. These materials include, but are not limited to, elastomeric sheets, polymeric films, and metal foils, e.g., aluminum foil, any of which may further include a reinforcing material. Further, the peel strip may be coated and/or impregnated with a biocide. Preferably, the peel strip is a sterile porous or microporous membrane, allowing steam to pass through during autoclaving, more preferably having a minimum tensile strength of about 60N.

Any of numerous seals may be provided on the face, including, for example, gaskets, resilient sealing members, or O rings. Preferably, the seal comprises a soft rubber or thermoplastic elastomer (TPE) (e.g., about 50 to about 65 shore A). As shown in FIGS. 1A and 2A, the flexible seal lips prevent environmental contamination from entering the connector assembly when the anti-actuation assembly is removed. Since the lips can flex and spring, the peel strips can be removed with reduced force, and the lips quickly close the gap. As shown in FIG. 2A, as the hollow bodies are moved (e.g., twisted) into the actuation position, the flexible lips (that are preferably narrow) quickly fold out of the way into a recess 123, 223 in each hollow body, wherein both the lips and the seal bodies (seal lozenges) contact each other, providing a more robust face seal, and the contact between the lozenges provides a face to face seal, preventing fluid leaks even under increases pressures (e.g., pressures up to about 4 barg).

If desired, and as shown in FIGS. 1B, 2B, 8A, 8B, 9A, and 9B, the first hollow connector body comprises a first connector external surface 175 (illustrated as part of a cover 180 on the first hollow connector body) further comprising a first alignment indicator 190; and the second hollow connector body comprises a second connector external surface 275 (illustrated as part of a cover 280 on the second hollow connector body) further comprising a second alignment indicator 290; the first alignment indicator and the second alignment indicator not aligning when the first hollow connector body and the second hollow connector body are in the first position (FIG. 8), and the first alignment indicator and the second alignment indicator aligning (FIG. 2B) when the first hollow connector body and the second hollow connector body are in the second (actuation) position.

To prevent inadvertent removal of or damage to the peel strips, each connector body may further comprise a removable cap which covers at least a substantial portion of the peel strip and the first end of the connector body. The cap can be fitted to the connector body at the first end, for example, by a friction fit or a snap fit, and may have any of a wide variety of configurations. For example, as shown in FIGS. 9A and 9B each cap 600, 700 may have a rigid top 601, 701 which protects at least part of the peel strip and a skirt 602, 702 which fits along the rim 119, 219 of the connector body 100, 200. The cap 600, 700 may also include handle 610, 710 as part of the skirt, or which extends axially below the skirt 602, 702. Preferably, as shown in FIGS. 9A and 9B, the cap includes a tear strip 615, 715 having a tear strip handle 616, 716, allowing the operator to grasp the tear strip handle and tear the tear strip, allowing the cap to be more easily removed from the connector body. The peal strip 520 (520A, 520B) may be bent axially under the handle 610, 710, and the handle may extend along all or at least a portion of the peal strip 520 (520A, 520B). The handle, tear strip, and/or tear strip handled may be used to lift the cap 600, 700 off of the connector body 100, 200 and may also prevent inadvertent manipulation of the anti-actuation assembly tab 501 and/or peel strip.

The components of the connector assembly can be sterilized as is known in the art (e.g., autoclaved, gamma irradiated, etc.)

The second ends of the hollow bodies may be connected to a fluid system and/or fluid treatment device, for example, via hoses, pipes, or other conduits, as is known in the art. Fluid may then flow through the connector assembly 1000 via the second end of either connector body, into the interior of one connector body and into the interior of the other connector body via the coaxially aligned openings 121, 221, exiting the connector assembly 1000 from the second end of the other connector body.

Typically, the second ends of the bodies include a fitting section may include any of a wide variety of fittings for coupling the body to a hose, pipe, tubing or other conduit of a fluid system, or to a fluid treatment device (such as, for example, a filter device). For example, the fitting may be configured as the flange of a Triclover fitting; or a hosebarb or sanitary end fitting as shown in many of the Figures. The fittings can have any suitable inside and/or outside diameter as is known in the art. Typical fittings include, for example, ¼", ⅜", ½", ⅝" hosebarb fittings and ½" sanitary end fittings, but other suitable fittings are known in the art.

If desired, connector bodies can be color coded (e.g., using colored covers fitted on the hollow bodies), allowing system customization and identification, which can reduce connection errors, including multi-connection errors (e.g., fluid systems, such as fluid systems including bioreactors, can include a plurality of connections, such as fluid inlet ports, drain ports, sampling ports, vent ports, etc.), wherein the colors can provide a visual labeling guide for the various connections.

Embodiments of the invention are suitable for use with a variety of bioreactors, and suitable bioreactors, e.g., including one or more walls and one or more ports are known in the art. For example, FIG. 10 shows an illustrative bioreactor (or bioprocessing unit) 2000, comprising a biocontainer or bioreactor bag 900 having an interior volume and comprising a top wall 901 (shown including a manifold 975), a bottom wall 902, and side walls 903, and a plurality of ports in one or more walls. The illustrated bioreactor includes a number of ports, including a drain port 951, liquid addition ports 952A, 952B, a gas inlet port 953, a sampling port 954, and a probe insertion port 955, and additional ports, as well as an agitator 1800 comprising an impeller 1700 comprising a hub 1750 and first, second, and third impeller blades and a housing assembly 1600, that can be used with connector body assemblies and connector bodies, which can involve a number of different connections, involving, for example, different size tubing, different containers and/or different devices. The use of color coded connector bodies can allow the operator to readily recognize the appropriate assemblies to be used and the appropriate connections to be made.

Illustratively, the illustrated liquid addition port 952A and probe insertion port 955 each have larger diameters than that of illustrated liquid addition port 952B, gas inlet port 953, and sampling port 954, and thus, connector assemblies placed in fluid communication with these ports (e.g., via flexible tubing (1100, 1101) connected to a fitting at a second end of a connector body and/or via direct connection with the second end of a connector body) would typically use different internal diameter fittings such as hosebarbs for connection to the respective different internal diameter tubing, and the different connector assemblies could include different colors (e.g., one color for use with gas or for sampling and/or having a specified fitting internal diameter, and another color for use with probe devices (e.g., shown as 1300) and/or having another specified fitting internal diameter).

If desired, the covers can be designed to include color specific keyways that will only accept the correct mating cover, further error proofing the connection process(es).

The connector bodies may be configured in any of numerous ways to conduct fluid through the interior of the connector body and isolate the fluid from the external environment. Either connector body may be a single piece or a multipiece structure and may have any of various shapes. For example a connector body may comprise a multipiece structure having a hollow, generally cylindrical shape defining a fluid flow path through the interior of the body between the first and second ends.

Although the hollow bodies as illustrated have a uniform inner diameter between the first and second ends, the inner diameter can vary along the axis of the body between the first and second ends. For example, a body may include a main barrel section with a uniform inner diameter, a guide section at the first end with a uniform inner diameter smaller than the inner diameter of the barrel section, and a fitting section which includes the second end and also has a uniform inner diameter less than or about equal to the inner diameter of the barrel section.

The components of the connector assembly may be formed from a wide variety of materials. For example, one or more of any one of the following: hollow connector body, connector body cover, locking mechanism, tab, and cap, may be made from any metallic material and/or polymeric material which is compatible with the fluid that will flow through the connector assembly. The metallic material may include, but is not limited to, a stainless steel. Preferably, the connector bodies, the locking mechanism, and the caps are made from polymeric material, and the polymeric material may include, but is not limited to, one or more of a polycarbonate, polypropylene, polyvinyl chloride, polyethersulphone, polyvinylidene fluoride, or polysulphone. For some embodiments, a transparent or translucent polymeric material may be selected. Typically, the hollow bodies, tabs, and connector body covers are formed from a rigid injection molded plastic, preferably a BPA-free plastic, such as polyethersulfone (PES), polycarbonate (PC), polysulfone (PSU), and polybutylene terephthalate (PBT), and the cap is made from a low density injection molded plastic such as TPE or polypropylene (PP).

The components may be fabricated in a variety of ways, including molding, machining, pressing, and stamping, and may be fashioned into subassemblies.

For some embodiments, one or both of the connector bodies may be integrally connected to, including integrally formed with, another component instead of being connected to a pipe, tube or other conduit. The component may include a flexible or rigid container, for example, a bag, a vessel, or a housing which may contain another element of the component, such as a sensor, a valve, or a filter (providing a filter device). For example, the connector bodies may be integrally connected to a component and may serve as an inlet and/or an outlet for the component. The container of the component may define a fluid flow path through the container from the inlet connector body to the outlet connector body, and the element within the container may be positioned in the fluid flow path, e.g., across the fluid flow path.

The connector bodies may be integrally connected to, for example, a container, or the housing of a device, in any of numerous locations on the container or housing. For example, one or both connector bodies may be integrally connected on the top, bottom, and/or side of the container or housing. To connect the component to the fluid system, each connector body integrally connected to the component may be coupled to a connector body of another device or conduit of a fluid system in the any of ways previously described. Fluid flow may then be established in either direction through the component, e.g., through a device, via the fluid system.

All references, including publications, patent applications, and patents, cited herein are hereby incorporated by reference to the same extent as if each reference were individually and specifically indicated to be incorporated by reference and were set forth in its entirety herein.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

The invention claimed is:

1. A connector assembly for making fluid connections comprising:
    (a) a first hollow connector body, the first hollow connector body comprising a first resilient deformable seal having a central aperture and a lip surrounding the central aperture; a first locking mechanism integrally formed with the first hollow connector body, the first locking mechanism comprising at least one lug including a slot, and at least one ramp; a first hollow connector first body end and a first hollow connector second body end;
    (b) a second hollow connector body, the second hollow connector body comprising a second resilient deformable seal having a central aperture and a lip surrounding the central aperture; a second locking mechanism integrally formed with the second hollow connector body, the second locking mechanism comprising at least one lug including a slot, and at least one ramp; a second hollow connector first body end and a second hollow connector second body end;
        (i) wherein the first hollow connector body and the second hollow connector body contact each other in a first position, and when subsequently twisted together, the first resilient deformable seal seals against the first hollow connector body, and the second resilient deformable seal seals against the second hollow connector body, in a second position, the second position comprising an actuation position;
    the connector assembly further comprising a removable anti-actuation assembly comprising at least one peel strip, interposed between the first hollow connector first body end and the second hollow connector first body end, wherein, when the first hollow connector body and the second hollow connector body contact each other in the first position, the anti-actuation assembly, when present, prevents forming the actuation position of the connector assembly, and when removed, allows forming the actuation position of the connector assembly.

2. The connector assembly of claim 1, wherein the anti-actuation assembly comprises a first surface facing the first hollow connector first body end and a second surface facing the second hollow connector first body end; and the connector assembly further comprises an alignment arrangement for mating the anti-actuation assembly with the first connector hollow body and the second hollow connector body, the alignment arrangement comprising protrusions and recesses;

wherein the first and second surfaces of the anti-actuation assembly, the first hollow connector first body end, and the second hollow connector first body end each have at least one protrusion and/or at least one recess, such that the first surface of the anti-actuation assembly mates with the first hollow connector first body end, and the second surface of the anti-actuation assembly mates with the second hollow connector first body end.

3. The connector assembly of claim 2, wherein the anti-actuation assembly comprises:

a first anti-actuation subassembly comprising the first surface of the anti-actuation assembly, and a first peel strip; and, a second anti-actuation subassembly comprising the second surface of the anti-actuation assembly, and a second peel strip.

4. The connector assembly of claim 3, wherein the first anti-actuation subassembly and the second anti-actuation subassembly are mated together when the first hollow connector body and the second hollow connector body contact each other in the first position.

5. The connector assembly of claim 4, wherein the first hollow connector body comprises a first connector external surface further comprising a first alignment indicator; and the second hollow connector body comprises a second connector external surface further comprising a second alignment indicator;

the first alignment indicator and the second alignment indicator aligning when the first hollow connector body and the second hollow connector body are in the actuation position.

6. The connector assembly of claim 3, wherein the first hollow connector body comprises a first connector external surface further comprising a first alignment indicator; and the second hollow connector body comprises a second connector external surface further comprising a second alignment indicator;

the first alignment indicator and the second alignment indicator aligning when the first hollow connector body and the second hollow connector body are in the actuation position.

7. The connector assembly of claim 2, wherein the first anti-actuation subassembly and the second anti-actuation subassembly are mated together when the first hollow connector body and the second hollow connector body contact each other in the first position.

8. The connector assembly of claim 2, wherein the first hollow connector body comprises a first connector external surface further comprising a first alignment indicator; and the second hollow connector body comprises a second connector external surface further comprising a second alignment indicator;

the first alignment indicator and the second alignment indicator aligning when the first hollow connector body and the second hollow connector body are in the actuation position.

9. The connector assembly of claim 1, wherein the anti-actuation assembly comprises:

a first anti-actuation subassembly comprising the first surface of the anti-actuation assembly, and a first peel strip; and, a second anti-actuation subassembly comprising the second surface of the anti-actuation assembly, and a second peel strip.

10. The connector assembly of claim 9, wherein the first anti-actuation subassembly and the second anti-actuation subassembly are mated together when the first hollow connector body and the second hollow connector body contact each other in the first position.

11. The connector assembly of claim 10, wherein the first hollow connector body comprises a first connector external surface further comprising a first alignment indicator; and the second hollow connector body comprises a second connector external surface further comprising a second alignment indicator;

the first alignment indicator and the second alignment indicator aligning when the first hollow connector body and the second hollow connector body are in the actuation position.

12. The connector assembly of claim 9, wherein the first hollow connector body comprises a first connector external surface further comprising a first alignment indicator; and the second hollow connector body comprises a second connector external surface further comprising a second alignment indicator;

the first alignment indicator and the second alignment indicator aligning when the first hollow connector body and the second hollow connector body are in the actuation position.

13. The connector assembly of claim 1, comprising a genderless connector assembly.

14. A fluid system comprising a connector assembly of claim 1, in fluid communication with a bioprocessing unit, the bioprocessing unit comprising a biocontainer having at least one wall including at least one port, an interior volume and including an impeller, wherein one of the first and second hollow connector bodies is in fluid communication with the port.

15. The connector assembly of claim 1, wherein the first hollow connector body comprises a first connector external surface further comprising a first alignment indicator; and the second hollow connector body comprises a second connector external surface further comprising a second alignment indicator;

the first alignment indicator and the second alignment indicator aligning when the first hollow connector body and the second hollow connector body are in the actuation position.

16. The connector assembly of claim 1, wherein the first hollow connector body comprises a recess and a seal body; and the second hollow connector body comprises a recess and a seal body; and when the first resilient deformable seal seals against the first hollow connector body, and the second resilient deformable seal seals against the second hollow connector body, in the second position, the lip of the first resilient deformable seal folds into the recess of the first hollow connector body and the lip of the second resilient deformable seal folds into the recess of the second hollow connector body, and the lip of the first resilient deformable seal contacts the lip of the second deformable seal, and the seal body of the first resilient deformable seal contacts the seal body of the second resilient deformable seal, providing a face to face seal.

17. A connector body for use in a connector assembly for making fluid connections comprising:
- a hollow connector body, the hollow connector body comprising a resilient deformable seal having a central aperture and a lip surrounding the central aperture; a locking mechanism integrally formed with the hollow connector body, the locking mechanism comprising at least one lug including a slot, and at least one ramp; a hollow connector first body end and a hollow connector second body end; and an anti-actuation assembly engagement portion comprising at least one recess and/or at least one protrusion;
- a removable anti-actuation assembly comprising at least one peel strip, and at least one recess and/or at least one protrusion, the at least one recess and/or at least one protrusion being engaged with the anti-actuation assembly engagement portion of the hollow connector body; and,
- a removable cap, engaged with the hollow connector body, wherein the removable anti-actuation assembly is interposed between the cap and the hollow connector first body end, the cap covering the hollow connector first body end.

18. A process for making fluid connections comprising:
(a) placing a first hollow connector body, the first hollow connector body comprising a first resilient deformable seal having a central aperture and a lip surrounding the central aperture; a first locking mechanism integrally formed with the first hollow connector body, the first locking mechanism comprising at least one lug including a slot, and at least one ramp; a first hollow connector first body end and a first hollow connector second body end; and a first hollow connector body anti-actuation assembly engagement portion comprising at least one recess and/or at least one protrusion; in contact with a second hollow connector body, the second hollow connector body comprising a second resilient deformable seal having a central aperture and a lip surrounding the central aperture; a second locking mechanism integrally formed with the second hollow connector body, the second locking mechanism comprising at least one lug including a slot, and at least one ramp; a second hollow connector first body end and a second hollow connector second body end; and a second hollow connector body anti-actuation assembly engagement portion comprising at least one recess and/or at least one protrusion; in a first position; wherein a removable anti-actuation assembly is interposed between the first hollow connector first body end and the second hollow connector first body end, the anti-actuation assembly comprising at least one peel strip, and at least one recess and/or at least one protrusion, the at least one recess and/or at least one protrusion being engaged with the first hollow connector body anti-actuation assembly engagement portion and the second hollow connector body anti-actuation assembly engagement portion; the anti-actuation assembly preventing formation of an actuation position of the connector assembly;

removing the anti-actuation assembly; and (b) twisting the first hollow connector body and/or the second hollow connector body such that the first locking mechanism engages with the second locking mechanism, the first resilient deformable seal seals against the first hollow connector body, and the second resilient deformable seal seals against the second hollow connector body, in a second position, the second position comprising the actuation position.

* * * * *